United States Patent
Pate (10) Patent No.: US 6,250,301 B1
(45) Date of Patent: Jun. 26, 2001

(54) VAPORIZER FOR INHALATION AND METHOD FOR EXTRACTION OF ACTIVE INGREDIENTS FROM A CRUDE NATURAL PRODUCT OR OTHER MATRIX

(75) Inventor: David W. Pate, Amsterdam (NL)

(73) Assignee: Hortal Harm B.V., Amsterdam (NL)

( * ) Notice: Subject to any disclaimer, the term of this patent is extended or adjusted under 35 U.S.C. 154(b) by 0 days.

(21) Appl. No.: 08/919,317

(22) Filed: Aug. 28, 1997

(51) Int. Cl.[7] ............................ A61M 16/00; F23D 11/00; F23D 14/00
(52) U.S. Cl. .............................. 128/203.26; 128/203.12; 128/203.27; 128/202.21; 128/204.13; 392/386; 392/390; 392/397; 96/361; 261/DIG. 65; 131/194; 239/136
(58) Field of Search ............................... 261/10 EG, 165, 261/DIG. 65, DIG. 165; 96/361, 363, 364; 55/503, 495; 128/203.12, 203.16, 203.17, 203.26, 203.27, 204.13, 202.21; 239/53, 55, 56, 57, 58, 59, 60, 135, 136, 325, 375, 338; 392/386, 390, 396, 397, 398; 131/194, 195, 198, 200, 330

(56) References Cited

U.S. PATENT DOCUMENTS

| 437,070 | | 9/1890 | Wiesebrock . | |
|---|---|---|---|---|
| 529,808 | * | 11/1894 | Ross | 128/204.13 |
| 649,521 | * | 5/1900 | Libbey | 128/203.26 |
| 659,188 | * | 10/1900 | Underwood | 128/203.26 |
| 676,713 | * | 6/1901 | Cross | 128/203.12 |
| 855,984 | * | 6/1907 | Russell | 128/204.13 |
| 1,009,929 | * | 11/1911 | Phillips | 128/204.13 |
| 1,071,389 | | 8/1913 | Blosser . | |
| 1,151,649 | * | 8/1915 | Barr | 128/203.27 |
| 1,405,802 | * | 2/1922 | Phelan et al. | 128/203.26 |
| 1,563,316 | * | 12/1925 | Anscombe | 128/203.17 |
| 2,644,799 | * | 7/1953 | Robinson | 252/455 |
| 2,808,494 | * | 10/1957 | Telkes | 219/19 |
| 3,152,240 | * | 10/1964 | Scott | 128/200.21 |

(List continued on next page.)

FOREIGN PATENT DOCUMENTS

| 19633401A1 | * | 2/1998 | (DE) | 128/203.12 |
|---|---|---|---|---|
| WO 99/11311 | * | 3/1999 | (WO) | 128/203.12 |

OTHER PUBLICATIONS

Clarke et al. Medical Marijuana. J. Int'l Hemp Assoc. 1: 9–12, Jan. 1994.*
Pate, D. W. Guide to the Scientific Literature on Potential Medical Uses of Cannabis and Cannabinoids, J. Int'l Hemp Assoc. 2(2): 74–76, Sep. 1995.*
Aromed Vaporizer Commercial Literature, Dec. 1999.*

*Primary Examiner*—Dennis Ruhl
*Assistant Examiner*—Joseph F. Weiss, Jr.
(74) *Attorney, Agent, or Firm*—Sughrue, Mion, Zinn, Macpeak & Seas, PLLC (57) ABSTRACT

A vaporizer apparatus and method for uniformly extracting active ingredients of a specimen of crude natural product or inert particulate matrix impregnated with volatile substances, without pyrolysis, which uses hot air or a heated inert gas stream to volatilize the specimen. The heated air or gas is introduced from below (from either a hot air gun or a high pressure tank connected to a heat exchanger) and ascends through a permeable support structure (e.g., fritted glass disk, etc.), subsequently causing specimen particles disposed on the permeable support structure to be suspended within the confines of an isolation chamber. This allows a maximized gas extraction exposure for each suspended particle, and promotes a uniform extraction of the aggregate charge through its periodic mixing. A filter prevents the particles from being inhaled by the user. During device disuse, the heated airstream flows through an optional side-arm of the vaporizer apparatus, preventing wasteful loss of active ingredients. In another embodiment, the side-arm can also be used to divert mixed purge gases from the specimen required to be under inert gas during its extraction.

25 Claims, 9 Drawing Sheets

U.S. PATENT DOCUMENTS

| | | | |
|---|---|---|---|
| 3,290,112 | * | 12/1966 | Gillenwater et al. ............ 239/55 |
| 3,704,748 | * | 12/1972 | Hapgood ............ 165/165 |
| 3,718,805 | * | 2/1973 | Posey ............ 219/305 |
| 3,835,293 | * | 9/1974 | McAllister ............ 219/300 |
| 3,851,146 | * | 11/1974 | Bennett ............ 219/300 |
| 3,864,544 | * | 2/1975 | Van Amerongen ............ 219/301 |
| 3,876,762 | * | 4/1975 | Rabussier et al. ............ 424/78 |
| 3,903,883 | * | 9/1975 | Pecina et al. ............ 219/497 |
| 3,948,445 | * | 4/1976 | Andeweg ............ 239/53 |
| 3,990,848 | * | 11/1976 | Corris ............ 21/126 |
| 4,035,451 | * | 7/1977 | Tringali ............ 261/101 |
| 4,096,868 | * | 6/1978 | Norman ............ 131/173 |
| 4,141,369 | | 2/1979 | Burruss . |
| 4,164,950 | * | 8/1979 | Bechtold ............ 131/194 |
| 4,178,334 | * | 12/1979 | Miller ............ 261/142 |
| 4,203,455 | * | 5/1980 | Byrd, Jr. ............ 131/173 |
| 4,214,146 | * | 7/1980 | Schimanski ............ 219/274 |
| 4,219,032 | * | 8/1980 | Tabatznik et al. ............ 131/170 |
| 4,291,838 | * | 9/1981 | Williams ............ 239/138 |
| 4,303,083 | * | 12/1981 | Burruss, Jr. ............ 131/271 |
| 4,360,018 | * | 11/1982 | Choksi ............ 128/205.12 |
| 4,383,377 | * | 5/1983 | Crafton ............ 34/60 |
| 4,468,372 | * | 8/1984 | Seifert et al. ............ 422/124 |
| 4,693,235 | * | 9/1987 | Vigneau et al. ............ 126/283 |
| 4,766,912 | * | 8/1988 | Hackman et al. ............ 131/296 |
| 4,903,850 | * | 2/1990 | Frank et al. ............ 219/271 |
| 5,086,766 | * | 2/1992 | Beacham ............ 128/203.27 |
| 5,115,975 | * | 5/1992 | Shilling ............ 239/55 |
| 5,133,042 | * | 7/1992 | Pelonis ............ 392/365 |
| 5,259,062 | * | 11/1993 | Pelonis ............ 392/365 |
| 5,376,338 | * | 12/1994 | Zlotnik ............ 422/124 |
| 5,514,346 | * | 5/1996 | Fujita ............ 422/124 |
| 5,547,616 | * | 8/1996 | Dancs et al. ............ 261/26 |
| 5,553,607 | | 9/1996 | Chiu et al. . |
| 5,564,442 | * | 10/1996 | MacDonald et al. ............ 131/194 |
| 5,700,430 | * | 12/1997 | Bonnema et al. ............ 422/125 |
| 5,732,685 | | 3/1998 | Metzger . |
| 5,819,756 | * | 10/1998 | Mielordt ............ 131/330 |
| 5,918,596 | * | 7/1999 | Heinonen ............ 128/204.21 |
| 5,932,147 | * | 8/1999 | Chen ............ 261/30 |
| 6,095,153 | * | 8/2000 | Kessler et al. ............ 131/194 |

* cited by examiner

VAPORIZER FOR INHALATION AND METHOD FOR EXTRACTION OF ACTIVE INGREDIENTS FROM A CRUDE NATURAL PRODUCT OR OTHER MATRIX

The present invention relates to a vaporizer for inhalation and a method for extraction of active ingredients from a crude natural product or other matrix, by means of an ascending airstream heated to the temperature appropriate to volatilize the molecules.

BACKGROUND OF THE INVENTION

The use of plants as medicinal agents has a long and successful history. The majority of medicines used today are either derived directly from plants or synthesized as variations on natural molecules. However, modern medical practice has, for the most part, abandoned the use of whole plant products because of objections concerning variability in concentration of active ingredients, and unpredictable rates of active drug release from orally ingested crude drugs. Even teas made from medicinal plants cannot fully overcome the latter objection, as the dose provided depends on compound solubility and the conditions of extraction. In addition, accurate self-titration of this dose cannot be expected to overcome either objection, considering the excessive time-lag between oral ingestion and the onset of action.

The best resolution of these problems is through pulmonary ingestion of vaporized compounds, if they are sufficiently volatile. This provides a more immediate means of relief and a more accurate method for dose self-titration, as well as allowing a means for applying compounds to the pulmonary tract itself, as is necessary with diseases such as bronchial asthma, etc. Pulmonary ingestion of drugs also circumvents the "first-pass effect" by which oral drugs are transferred from the intestines and then partially or entirely metabolized by the liver, before entering the blood stream.

Unfortunately, the only technique available to accomplish pulmonary application of crude natural drugs has been via the method of smoking. This is objectionable from the medical perspective because pyrolysis products are irritating and long-term ingestion of smoke has been implicated in the etiology of various pulmonary disease states (e.g., emphysema, cancer, etc.).

Other objections to inhalers such as U.S. Pat. No. 87,603 (Tichenot) which continuously heats or pyrolizes a substance on a grating, and U.S. Pat. No. 1,858,580 (Collins) which steam heats a carrying agent permeated with a medicated substance, involve the lack of ability to either maximize the extraction exposure of the specimen particles, or to promote a uniform extraction of the aggregate charge through its periodic mixing. Additionally, prevention of large particle inhalation which may prove irritating to the pulmonary system of the user, and providing a demand-only flow of heated gas upon each inhalation, which spares wasteful loss of active ingredient during periods of device disuse, is not achieved.

SUMMARY OF THE INVENTION

An object of the present invention is to provide a vaporizer and a method by which a hot gas stream vaporizes and uniformly extracts the active ingredients of a crude natural product or products without pyrolysis, thereby avoiding the potentially detrimental effects of smoking.

A further object of the present invention is to spare the wasteful loss of active ingredients extracted by the vaporizer due to a continuous gas flow instead of a demand-only gas flow, and also to prevent the inhalation of large particles by the user due to a lack of a filtering mechanism.

A still further object of the present invention is to prevent clogging of the vaporizer apparatus due to evaporated compounds condensing on the permeable support structure of the vaporizer apparatus.

The present invention extracts volatile active ingredients from a crude natural product, as well as other volatile substances (e.g., essential oils) impregnated into an inert matrix (e.g. paper), by means of a moving airstream heated to the temperature appropriate to volatilize the molecules of the product or substance. Transfer of these agents or ingredients as a water-free aerosol is simultaneously accomplished by this same airstream. In addition, the means of introducing the heated gas into the pulverized crude drug from below provides for the solid particulates to be suspended in the airstream, completely exposing them to the extractive gases, as well as causing a mixing of the aggregate charge upon each inhalation.

In cases where prevention of labile active compound denaturation (e.g., oxidation) is required, the substitution of a stream of hot inert gas (e.g., helium, argon) for the stream of hot air can be implemented. The use of helium carries the additional advantage of raising the voice pitch of the inhaler, reminding the user that air has not been inhaled.

Upon each inhalation, the heated gas is introduced from below and ascends through a permeable support structure (e.g., fritted glass disk, etc.), subsequently causing specimen particles to be suspended within the confines of the isolation chamber. This allows a maximized gas extraction exposure for each suspended particle and promotes a uniform extraction of the aggregate charge through its periodic mixing. In addition, this method ensures that the support structure is kept clean and unclogged, since evaporated compounds are constantly swept away from its upper surface. A filter provided downstream from the permeable support structure prevents large particles from being inhaled by the user.

During device disuse in one embodiment, the heated airstream flows through a side-arm of the vaporizer apparatus, preventing wasteful loss of active ingredients. In another embodiment, the side arm can also be used to divert mixed purge gases from the specimen, when the specimen is required to be under the flow of inert gas during its extraction.

BRIEF DESCRIPTION OF THE DRAWINGS

Other features and advantages of the invention will be apparent from the following description taken in connection with the accompanying drawings, wherein.

DETAILED DESCRIPTION OF THE PREFERRED EMBODIMENTS

Figure 1:
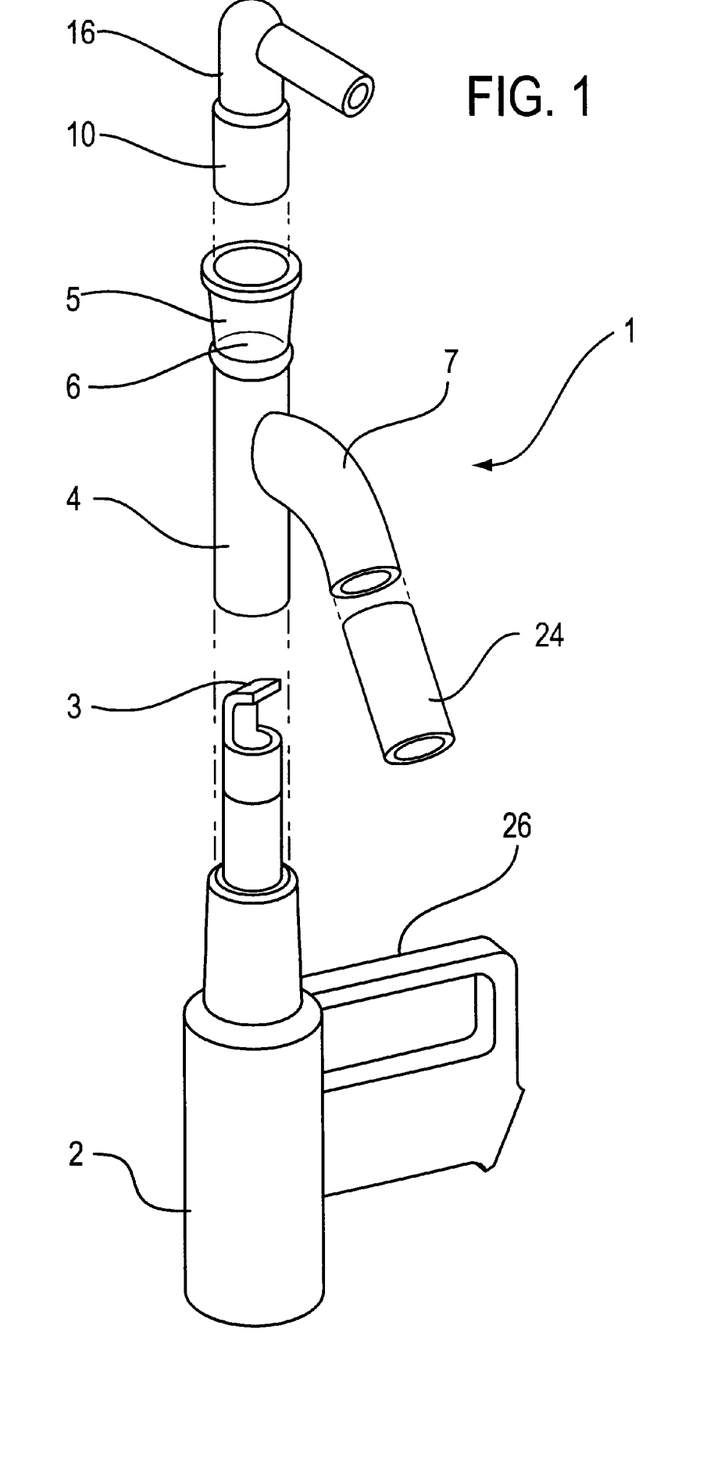
FIG. 1 shows an exploded view of the completed assembly of the vaporizer apparatus according to a first embodiment of the invention.
Figure 2:
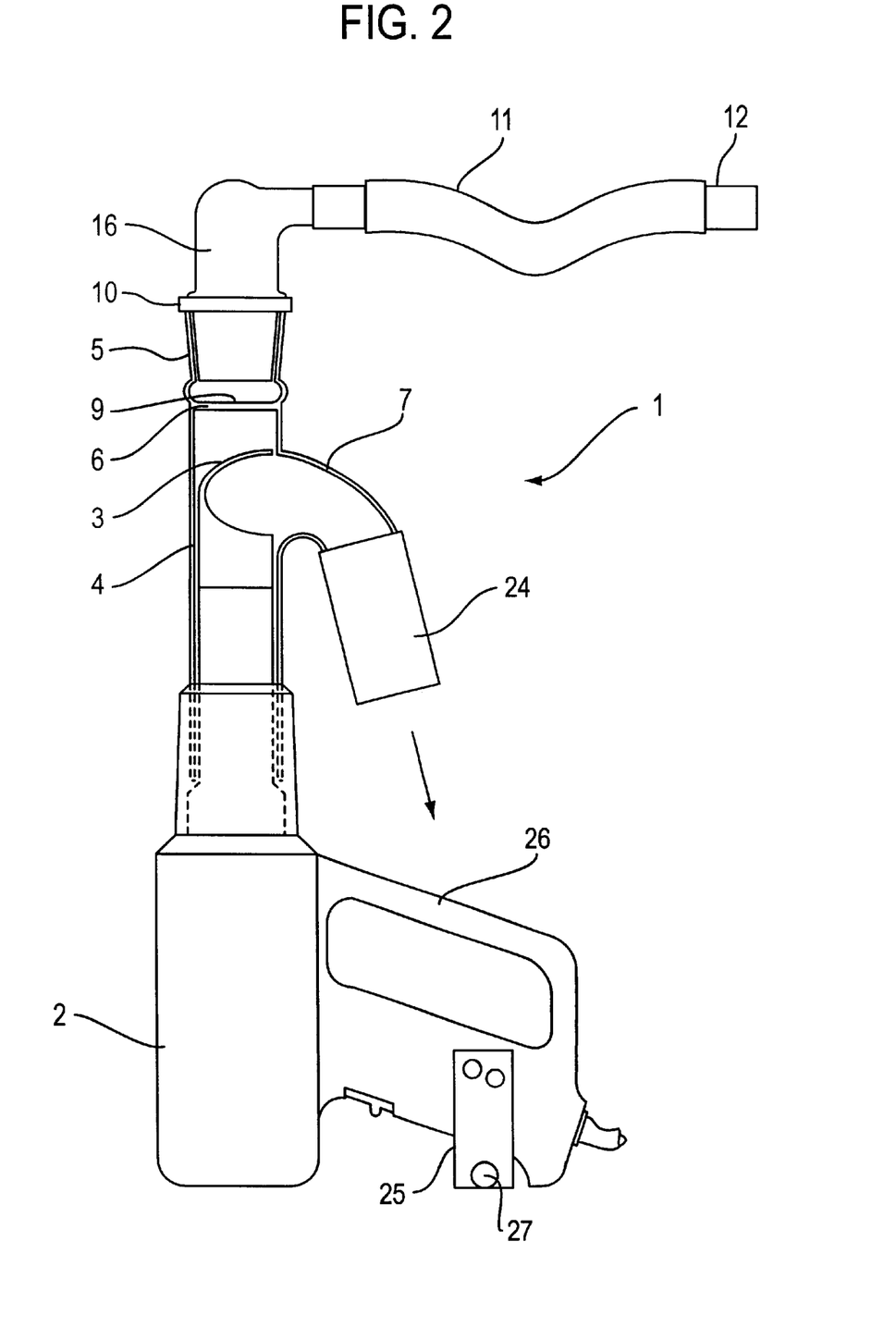
FIG. 2 shows the completed assembly of the vaporizer apparatus according to a first embodiment of the invention.

A completed assembly of the first embodiment of the vaporizer apparatus 1 of the present invention is shown in FIG. 2, with an exploded view shown in FIG. 1. The vaporizer apparatus 1 is mounted on a source of hot air 2 (e.g., Bosch Model 1943 or Model PHG 630-2 LCE hot air gun), and includes an optional internal diverter 3, which acts as a baffle-cum-brace within a glass tubing 4 which connects the source of hot air 2 to an isolation chamber 5 containing a permeable support structure 6 (e.g., fritted glass disk), and to a side-arm 7. The optional internal diverter 3, which increases efficiency if used, is fitted on the source of hot air 2 in order to secure the vaporizer apparatus 1 to the hot air source 2. When the user inhales, the partial vacuum created allows hot air to stream past the curved section of the upper portion of the diverter 3 through the permeable support structure 6. Between inhalations, the diverter 3 acts as a baffle, encouraging hot air to stream out through the side-arm 7 rather than flowing upward through the permeable support structure 6.

The isolation chamber 5 holds the specimen particles 8 (see FIGS. 3A and 3B) on the surface 9 of the permeable support structure 6. The permeable support structure 6 is fixed to the walls of the glass tubing 4. A disk filter screen 10 is disposed above, or downstream of the isolation chamber 5, and a tubing 11 (see FIG. 2) leads from the disk filter screen 10 to a mouthpiece 12 or a mask (not shown) through which the user inhales. The tubing 11 may be corrugated which allows flexing of the tube without kinking (not shown).

The side arm 7 (see FIGS. 1 and 2) provides means to duct the heated air stream away from the permeable support structure 6 when the vaporizer apparatus 1 is not in use (e.g., when the user is resting between inhalations). The side arm 7 can be equipped with a valve 24 to manually re-route the entire heated airstream through the permeable support structure 6 for ancillary purposes such as device cleaning, or as a room vaporizer, upon removal of tubing 11. As an example, the valve 24 could be provided with either a silicone stopper or, alternatively, could be manually clamped by a hemostat, pinchcock or other similar compression device (not shown). The wall thickness of this short piece of silicone tubing also provides the user insulation from the hot glass side arm 7 underneath it.

Figure 4:
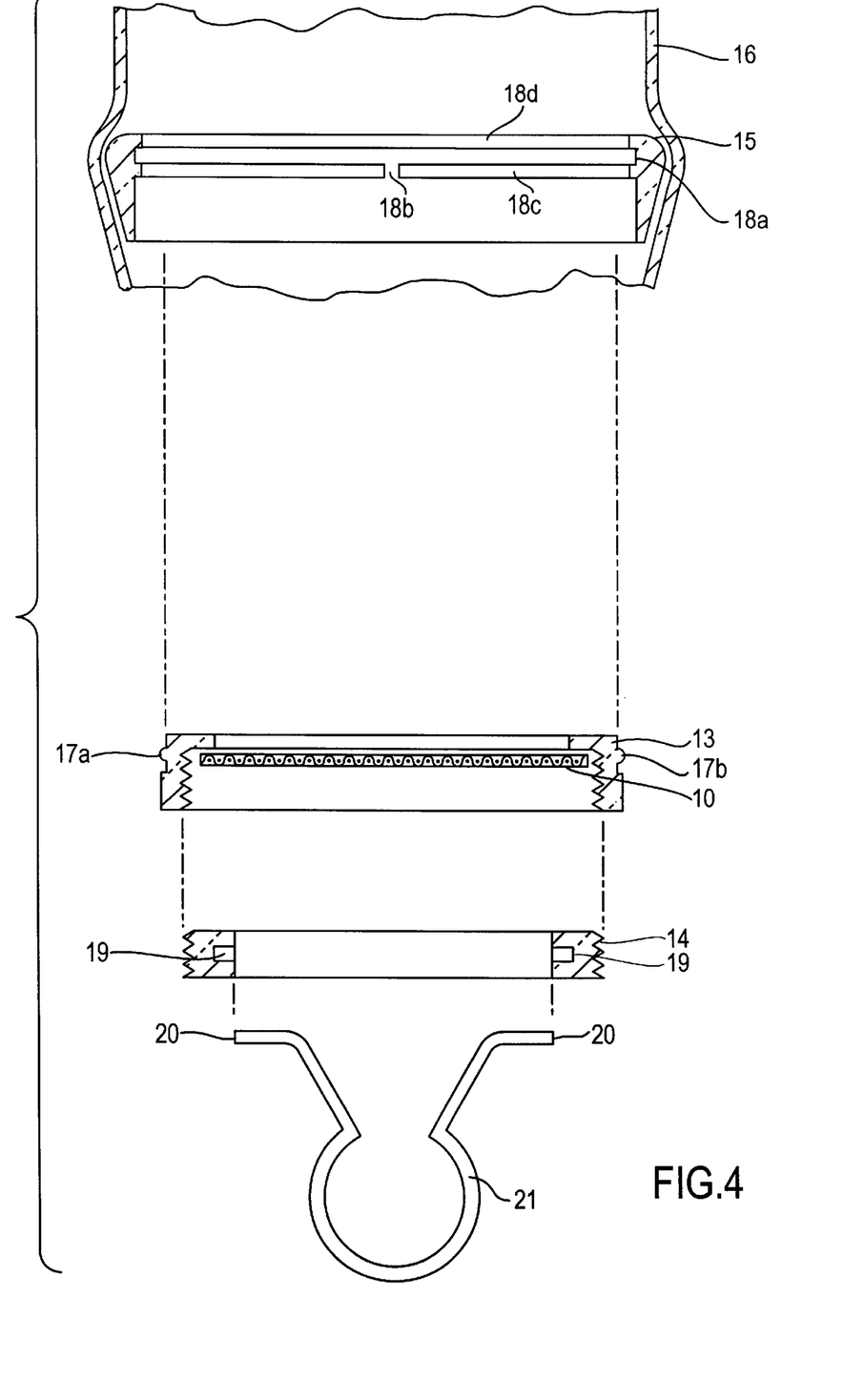
FIG. 4 shows the disk filter screen retention assembly of the vaporizer apparatus and a metal clip removal tool.

FIG. 4 shows the disk filter screen retention assembly. In order to assemble the disk filter screen retention assembly, the disk filter screen 10, which is made of a finely meshed material (e.g., stainless steel), is first seated in an outer filter retention ring 13. Then, the arms 20 of a metal clip tool 21 are inserted into holes 19 which are located in the inner peripheral surface of inner filter retention ring 14, and disposed directly across from one another. The inner filter retention ring 14 is then threaded into the outer filter retention ring 13 by turning the tool 21 to tighten the inner filter retention ring 14 within the outer filter retention ring 13 and keep the disk filter screen 10 stable between the two structures 13, 14.

Next, the outer filter retention ring 13 is inserted into an interface ring 15 made of a heat-resistant synthetic material (e.g., fluorocarbon). The interface ring 15 is provided in the lower portion of a glass headpiece 16, which fits onto the upper portion of the glass tubing 4. The interface ring 15 is laterally compressed into an ovoid shape and is inserted through the bottom of the glass headpiece 16. Interface ring 15 includes an upper lip 18d, a lower lip 18c, a groove 18a, and gap 18b within the lower lip 18c of the groove 18a, all within its inner periphery, which are operative to provide a locking fit to the outer filter retention ring 13.

Namely, pins 17a, 17b, which are disposed on the outer peripheral surface of the outer filter retention ring 13, are aligned with gap 18b of groove 18a of the interface ring 15, and are inserted through the gap 18b into the groove 18a and the subassembly of the outer filter retention ring 13, inner filter retention ring 14, and disk filter screen 10, is turned using the tool 21, to provide a locking fit of the subassembly within the interface ring 15 (bayonet-type coupling).

To remove the disk filter screen retention assembly, the steps above are conducted in reverse order.

Figure 5:
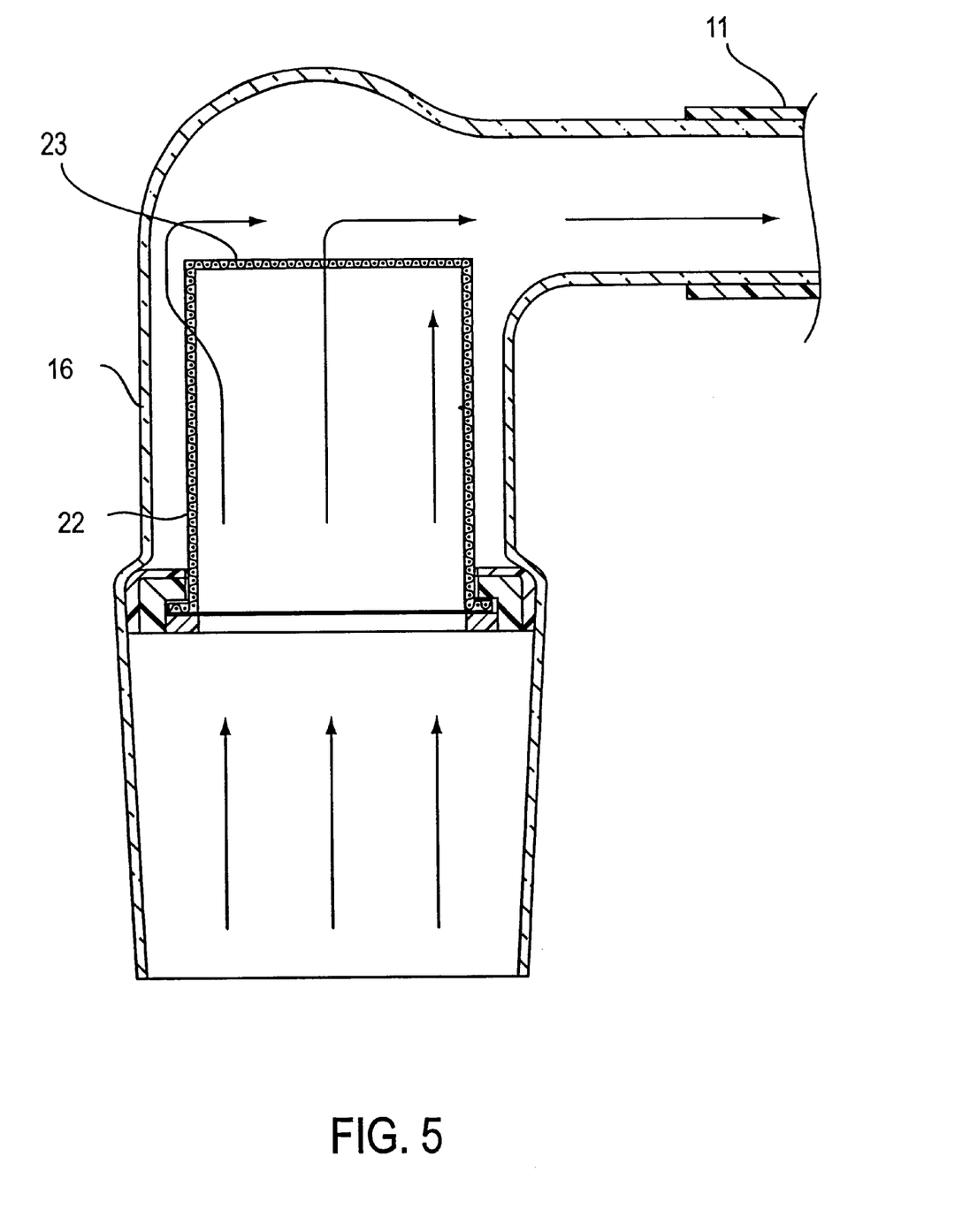
FIG. 5 shows the hollow cylindrical filter screen of the invention.
Figure 6:
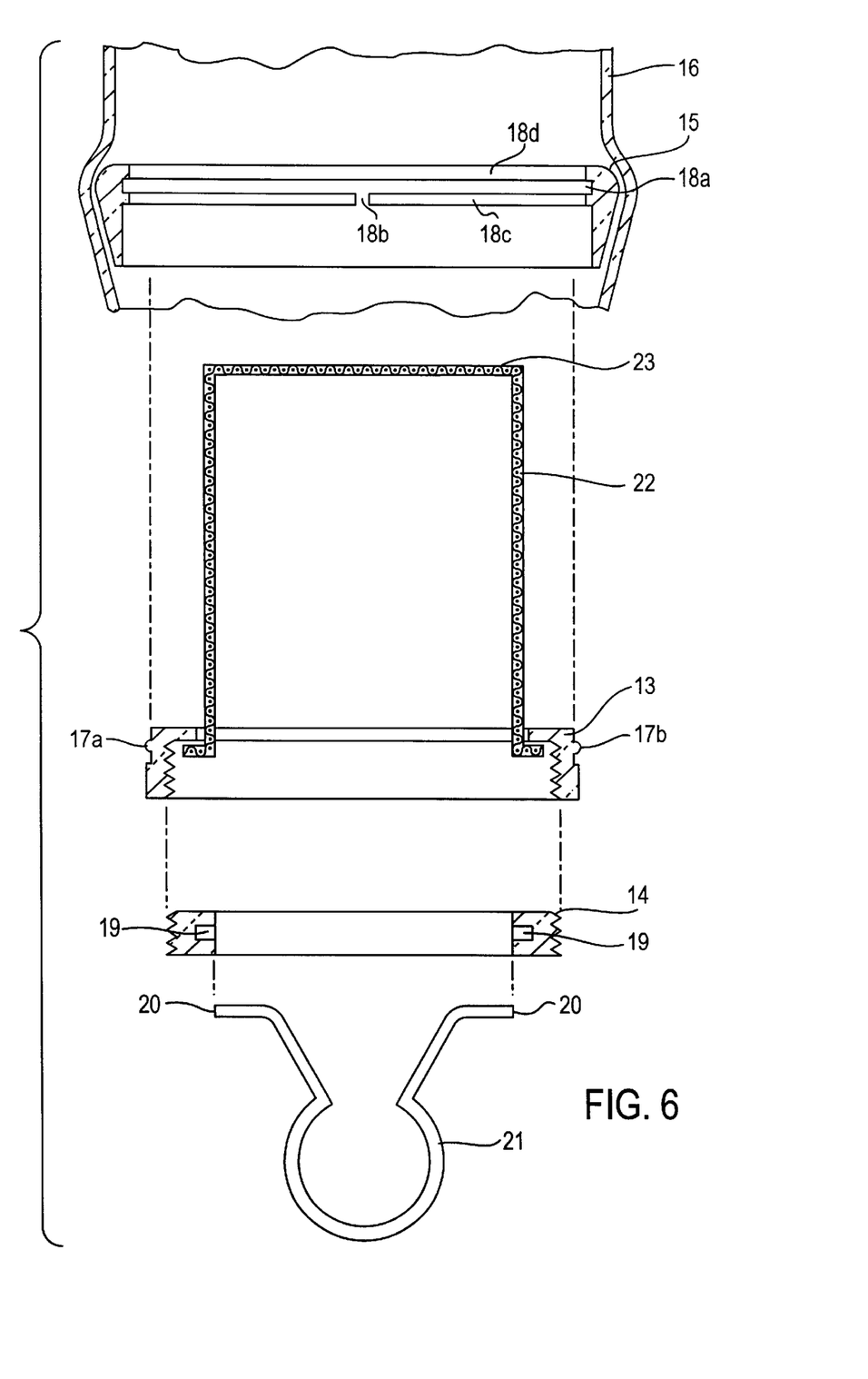
FIG. 6 shows the assembly of the hollow cylindrical filter screen of the vaporizer apparatus and a metal clip removal tool.
Figure 7A:
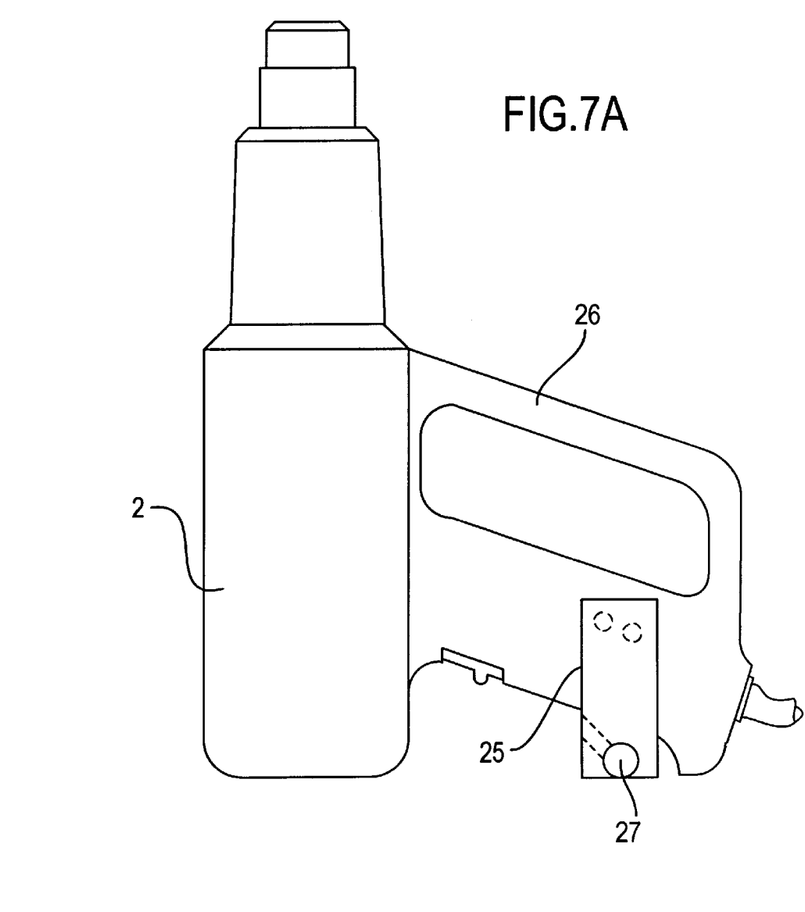
FIGS. 7A and 7B show the hot air gun with cradle and rod assembly of the vaporizer apparatus.
Figure 7B:
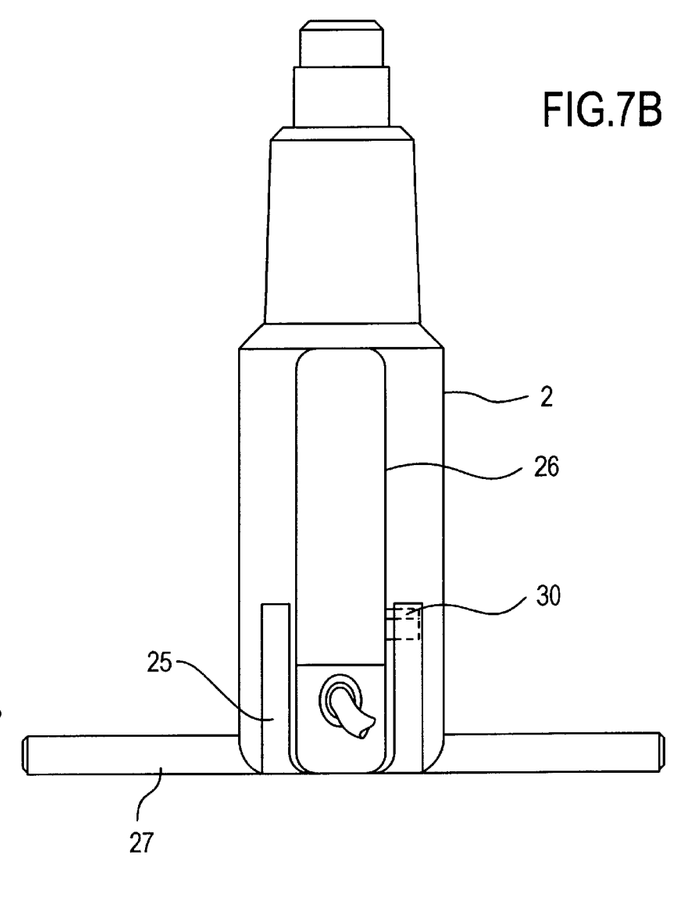
Figure 8:
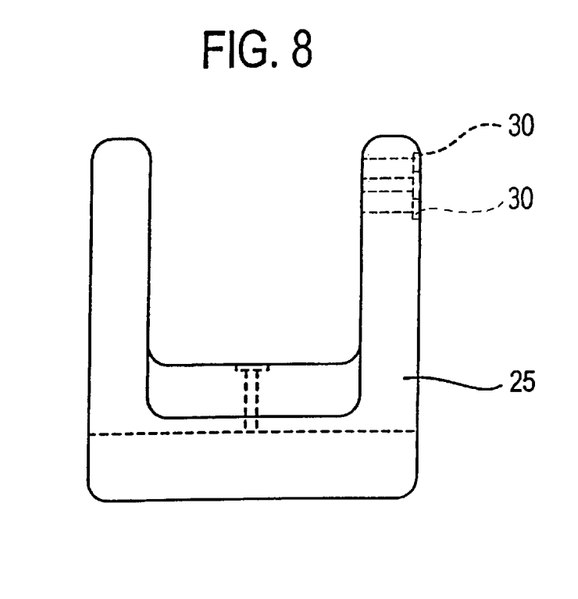
FIGS. 8, 9, and 10, show a more detailed view of the cradle and rod assembly of the vaporizer apparatus.
Figure 9:
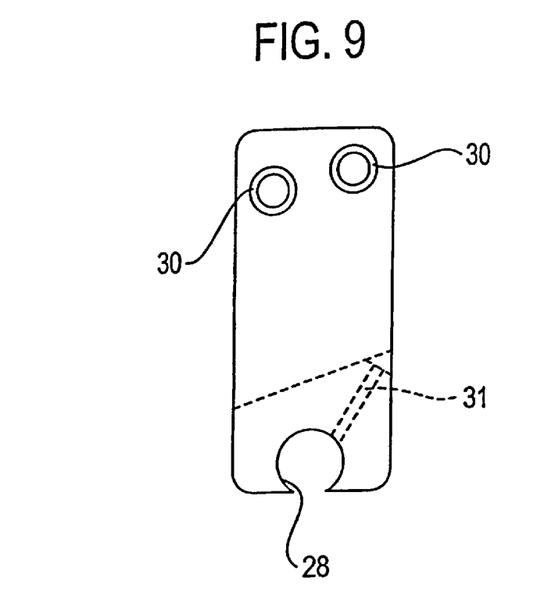
Figure 10:
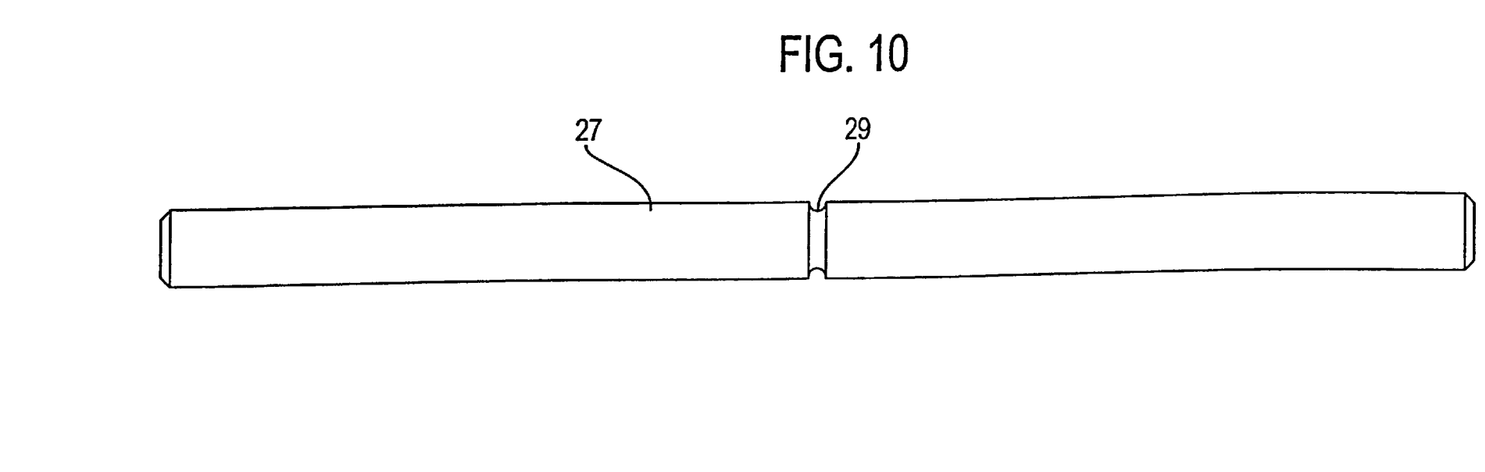

A hollow cylindrical filter screen 22, shown in FIG. 5, can be used as an alternative to the disk filter screen 10, in order to increase the surface area of the filtering means and provide additional height for specimen particles 8 to ascend from their origin on the surface 9 of the permeable support structure 6. The cylindrical filter screen 22 is made of a meshed material (e.g., stainless steel), and is assembled within the inner filter retention ring 14 and outer filter retention ring 13 as shown in FIG. 6 (like elements being denoted by like reference numerals), in the same manner as the disk filter screen 10, discussed above. The closed top portion 23 of the hollow cylindrical filter screen 22 can have any shape, including a domed, conical or flat surface.

The vaporizer apparatus 1 (see FIGS. 7A–10) is supported by a support cradle 25, which can be semi-permanently attached by screws or the like, mounted in threaded holes 30 and fixed to the handle 26 of a hot air gun 2. The support cradle 25 accommodates an easily mountable/demountable rod 27 via a rod receiving channel 28 disposed in the lower portion of the support cradle 25. A receiving groove 29 fixes rod 27 via a spring-ball screw or the like, mounted in threaded hole 31. Accordingly, by using the support cradle 25 and rod 27 apparatus, the entire vaporizer apparatus 1 can be laterally stabilized. Removal of the rod 27 allows flat storage of the vaporizing apparatus 1 or alternative uses of the hot air gun 2 itself in a variety of unrelated hand-held applications.

The operation of the present invention, with respect to the first embodiment shown in FIGS. 1 and 2, begins when the glass headpiece 16 of the isolation chamber 5 is removed and a small charge of specimen particles 8 (crude natural product or inert particulate matrix impregnated with the desired compounds) is placed in the isolation chamber 5, and the glass headpiece 16 replaced to close the isolation chamber 5.

The source of hot air (e.g., hot air gun) 2 is then turned on to bring the air-stream to the proper predetermined temperature. The source of hot air 2 provides a heated gas flow, which the internal diverter 3, acting as a baffle, routes through the side-arm 7. Inhalation provides the drop in pressure necessary to re-route a portion of the heated gas stream past the internal diverter 3 and through the permeable support structure 6. The proper predetermined working temperature of the air stream through the vaporizer apparatus 1 will vary according to the nature of the materials being volatilized, from approximately 50 to 250 degrees Celsius, but it is generally in the 100 to 200 degree Celsius range.

Inhalation draws a portion of the diverted hot airstream upwards through the permeable support structure (e.g., fritted glass disk) 6, to enter the isolation chamber 5 under the specimen charge.

Figure 3A:
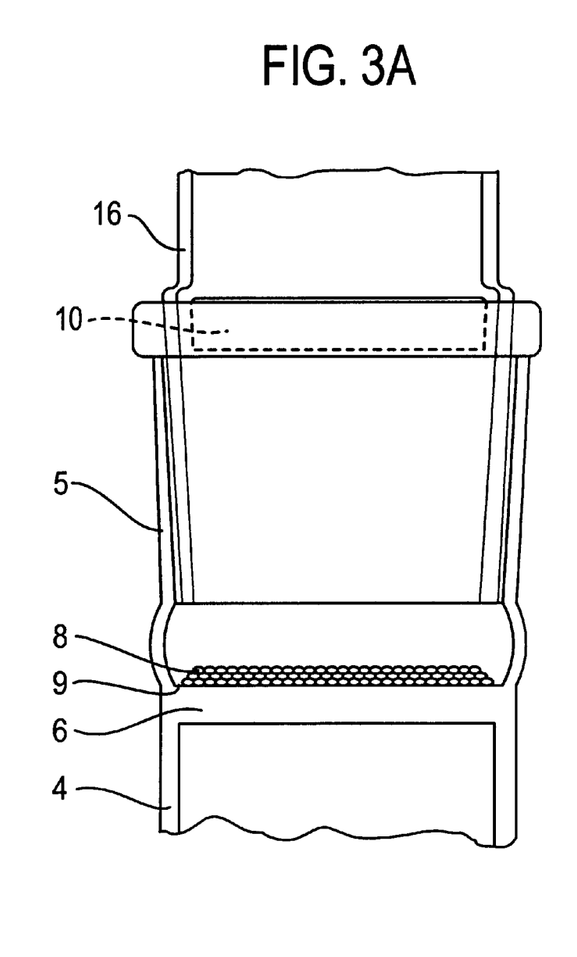
FIG. 3A shows the isolation chamber of the vaporizer apparatus with the specimen particles in their normal state.
Figure 3B:
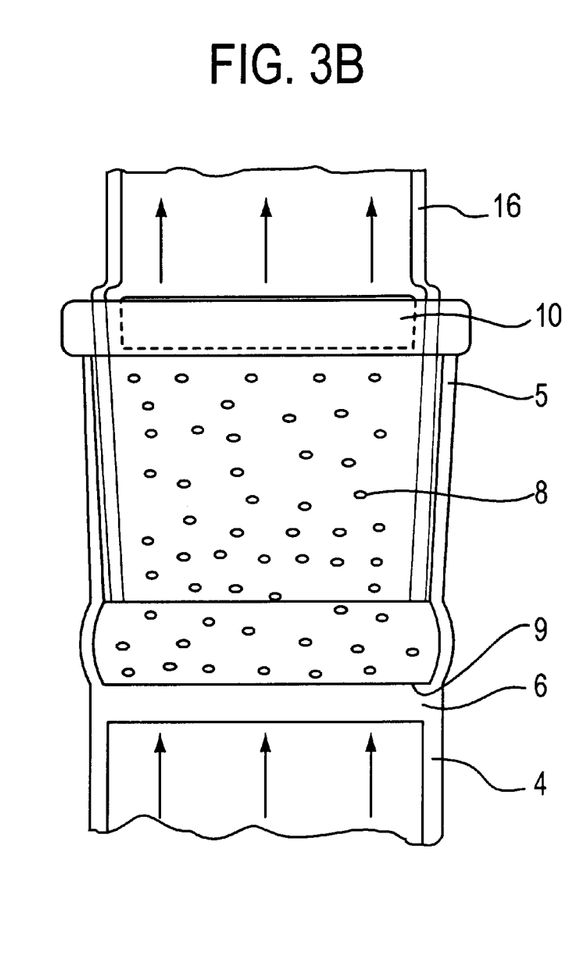
FIG. 3B shows the isolation chamber of the vaporizer apparatus with the specimen particles suspended by the ascending heated gas flow through the isolation chamber.

The aggregate charge is suspended as a cloud of particles 8, completely exposing each component particle to the extractive stream of hot air (see FIG. 3B). Accordingly, volatile components of the specimen are vaporized from the suspended specimen particles 8 by the hot air and this vapor is drawn into the pulmonary tract by inhaling, via the tubing 11 through the mouthpiece 12 or a mask (not shown).

Cessation of inhalation stops the upward flow of heated air through the chamber and allows gravity to collapse the cloud of suspended particles 8 back into its original state as a layer on the surface 9 of the permeable support structure 6 (see FIGS. 3A and 3B).

Backflow of outside unheated air through the side arm 7 during inhalation is avoided due to an overpressure maintained by the source of hot air 2 that is in excess of the pressure removed by the inhalation.

Inhalation of large particles 8 is prevented by the filter screen 10 disposed above the isolation chamber 5.

When not in active use, the system functions to allow the air and, therefore, the entire vaporizer apparatus 1, to maintain its optimal temperature, while avoiding a constant flow of heated gas through the specimen particles 8 whose active ingredients are to be extracted. This bypass effect is interrupted only on demand by inhalation, thereby sparing wasteful loss of active ingredients during periods of device disuse.

The disk filter screen 10 is self-cleaned at the end of each inhalation, of most specimen particles 8 by this same gravitational action. However, a sharp momentary exhalation into the tubing 11 also helps to force most residual specimen particles 8 away from the disk filter screen 10.

The exhausted charge of specimen particles 8 is emptied from the vaporizer apparatus 1 by turning off the heat source air flow, removing the glass headpiece 16 from the top of the isolation chamber 5 and then either scooping or vacuuming out the contents, or by lifting the cooled glass tubing 4 from the source of hot air 2 and inverting the vaporizer apparatus 1 to empty the contents of the isolation chamber 4. The specimen particles 8 may also be removed by simply lifting the glass headpiece 16 while sharply inhaling, thereby ensuring particles are adherent on the disk filter screen 10.

Figure 11:
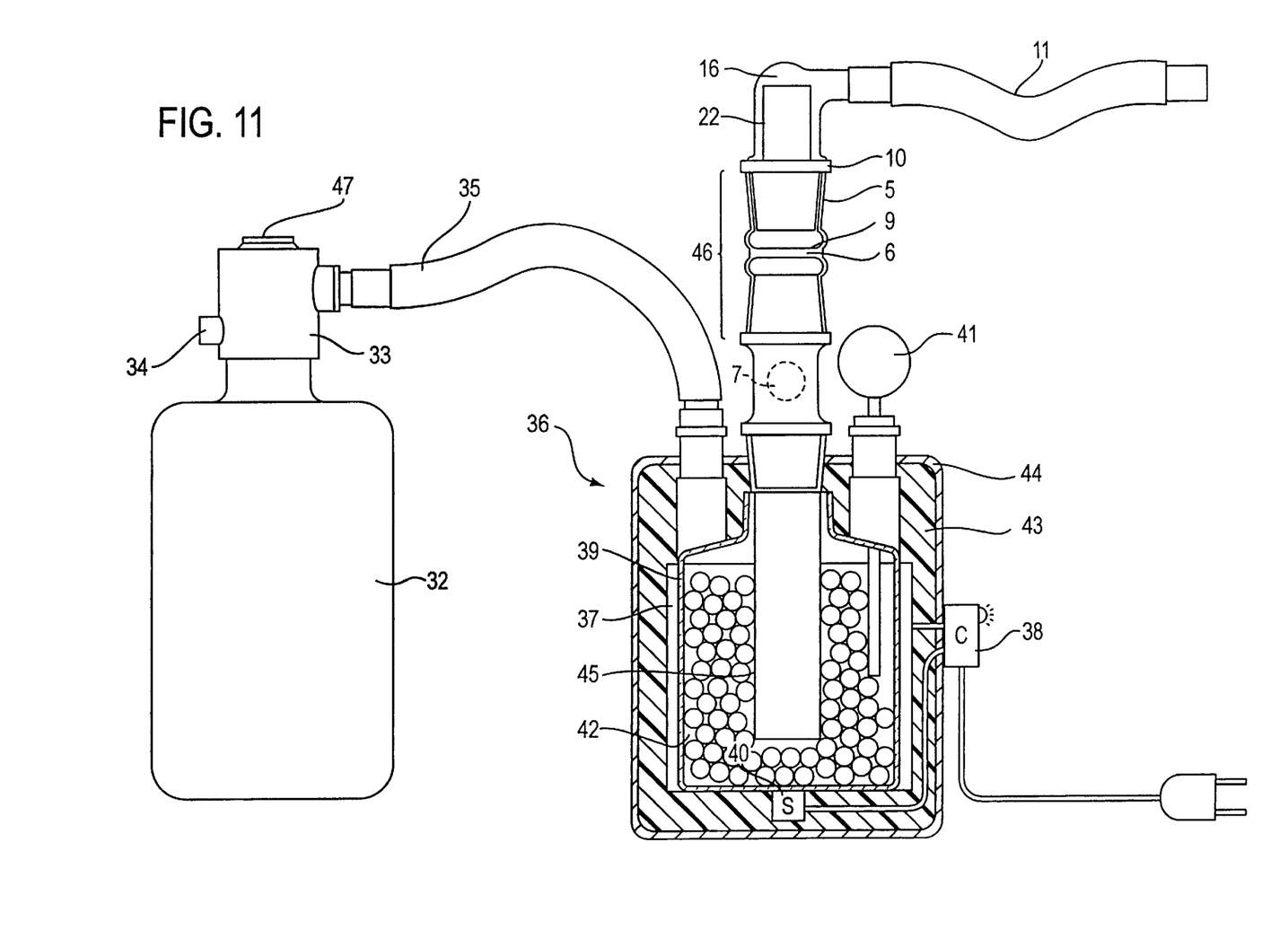
FIG. 11 shows the completed assembly of the vaporizer apparatus according to a second embodiment of the invention.

In a second embodiment of the present invention as shown in FIG. 11, a heated inert gas (i.e., helium, argon) is used instead of heated air. The heated inert gas is used to evaporate volatile compounds from their matrix in order to prevent their decomposition due to exposure to atmospheric gases (e.g., oxygen). Again, like elements are denoted by like reference numerals.

The second embodiment of the vaporizer apparatus 1 (see FIG. 11) includes a high pressure tank 32 of inert gas equipped with a demand-type SCUBA regulator 33 equipped with a refill port 34. A hose or tubing 35 from this regulator 33 is routed to a heat-exchange device 36. The heat exchange device 36 includes a heating band 37 or other resistance heating device made of metal, silicone, or other material, that generates heat from electrical input. A thermostatic control 38 regulates the electrical input to the heating band 37 so that the chamber or vessel 39 contained within the heat exchange device 36 is limited to a desired predetermined range of temperatures. A thermostatic sensor 40 acts as a heat detection device that determines the temperature of the heated vessel 39, and transmits the data to the thermostatic control 38. A thermometer 41 measures the internal temperature status of the contents of the vessel 39, and provides visual feedback to the user.

The heating band 37 heats the heat exchange spheres 42, which are made of metal, glass, ceramic, or other suitable material. The heat exchange spheres 42 provide a large surface area upon which the percolating gases can be instantaneously heated.

The insulation 43 surrounding the vessel 39 of the heat exchange device 36 is made of glass, ceramic, or other suitable material, and traps the heat generated by the heating band 37 to ensure temperature stability for the heat exchange spheres 42. The insulation 43 is normally contained within an outer protective casing 44 made of metal or other material.

A vertical pipe 45 disposed within the vessel 39 amongst the heat exchange spheres 42, and which has an upper portion which projects upwardly out of the heat exchange device 36, has a glass tubing 46 fitted over its upper portion. The glass tubing 46 contains an isolation chamber 5, the lower portion of which seats a permeable support structure 6. A glass headpiece 16 is fitted into the isolation chamber 5.

As with the first embodiment, the isolation chamber 5 holds the specimen particles 8 (see FIGS. 3A and 3B) on the surface 9 of the permeable support structure 6. The permeable support structure 6 is fixed to the walls of the glass tubing 46. A filter screen 10 is disposed above, or downstream of the isolation chamber 5, and a tubing 11 leads from the filter screen 10 to a mouthpiece 12 or a mask (not shown) through which the user inhales. As with the first embodiment, the tubing 11 may be corrugated (not shown) which allows flexing of the tube without kinking. A hollow cylindrical filter screen 22 can be used instead of the disk filter screen 10.

In initial operation of the invention with respect to the second embodiment, the demand-type pressure regulator 33 of the tank 32 of inert gas, is first opened via its purge valve 47 so that the gas flows through the tubing 35 into the heat exchange vessel 36 and then out via side arm 7 opening. Side arm 7 is then blocked by suitably clamping (not shown) the attached silicone tubing 24 (see FIG. 2). 11, purging residual air in the vaporizer apparatus 1.

Once in the heat exchange device 36, the inert gas is heated by heat exchange spheres 42 in the heat exchange vessel 39 to the proper predetermined temperature. After charging the isolation chamber 5 with a specimen to be extracted (crude natural product or inert particulate matrix impregnated with the desired compounds), inhalation draws additional inert gas from the pressure tank 32 via the heat exchange device 36. The heated inert gas proceeds upwards through the vertical pipe 45 and through the permeable support structure 6, entering the isolation chamber 5 which contains the charge of specimen particles 8. The remaining structure and steps in the procedure are the same as that described above with the first embodiment.

In the second embodiment of the invention, side-arm 7 venting of gas is not absolutely necessary. However, if the isolation chamber 5 is to be charged with specimen particles 8 before the purging of residual air from the heat exchange vessel 39, a manually valved side-arm 7 venting feature is useful to prevent heated mixed gases from sweeping over the specimen particles 8 until the system is free of air.

Removal of the exhausted charge of specimen particles 8 is initiated by removing the glass headpiece 16 from the top of the isolation chamber 5. The cooled glass tubing 46 that houses the permeable support structure 6 can then be removed from the glass tubing 45 and inverted to empty its contents resting on the surface 9. All the other removal techniques discussed above with respect to the first embodiment, can also be used.

It is contemplated that numerous modifications may be made to the apparatus and procedure of the invention without departing from the spirit and scope of the invention as defined in the following claims.

What is claimed is:

1. An apparatus for extracting active ingredients from a specimen of at least one of a crude natural product and an inert particulate matrix, comprising:

means for providing an ascending heated gas stream such that said specimen is heated by said heated gas stream to a predetermined temperature wherein said active ingredients of said specimen are volatilized;

means for isolating said specimen such that particles of said specimen are suspended within a predetermined area by said heated gas stream while said specimen is heated to said predetermined temperature during apparatus use, said isolation means being disposed downstream from said heating means;

means for filtering said particles of said specimen provided downstream from said isolation means, such that during inhalation by a user of said active ingredients of said specimen, said particles of said specimen are not inhaled by said user after said active ingredients of said specimen have been volatilized within said isolation means by said heating means; and means for diverting said heated gas stream away from said specimen during intermittent periods of apparatus disuse by said user, said diverting means being provided downstream from said heating means.

2. The apparatus according to claim 1, wherein said heated gas stream is comprised of one of air and an inert gas.

3. The apparatus according to claim 1, wherein said heating means comprises a hot air gun.

4. The apparatus according to claim 1, wherein said isolation means comprises:

a permeable support structure which provides upstream physical support for said unsuspended specimen during apparatus disuse.

5. The apparatus according to claim 4, wherein said permeable support structure comprises a fritted glass disk.

6. The apparatus according to claim 1, wherein said filter means comprises:

a screen made of a meshed material to prevent said suspended particles of said specimen from being inhaled by said user during apparatus use, and prevents downstream loss of suspended particles of said specimen during apparatus use.

7. The apparatus according to claim 1, wherein said heating means comprises:

a heat exchanger including:

a plurality of heat exchange spheres for transferring heat to said heated vapor stream;

a vessel for holding said plurality of heat exchange spheres;

a heating band surrounding said vessel, such that said heating band generates heat to said vessel from an electrical input, said heat being transferred from said vessel to said heat exchange spheres;

a thermostatic sensor for detecting a temperature within said vessel;

a thermostatic control that regulates said electrical input to said heating band based on data transmitted from said thermostatic sensor such that said predetermined temperature is achieved and maintained;

an insulation surrounding said heating band which traps heat within said vessel generated by said heating band to ensure temperature stability for said heat exchange spheres;

an outer casing surrounding said insulation; and a pipe disposed within said vessel amongst said heat exchange spheres, such that after said heat exchange spheres heat said gas stream within said vessel, said heated gas stream passes downstream to said isolation means via said pipe.

8. The apparatus according to claim 7, wherein said heat exchanger further comprises a thermometer for visual reading of said temperature by said user.

9. The apparatus according to claim 7, wherein said heated gas stream comprises:

an inert gas, said inert gas being provided from a high pressure tank having a SCUBA regulator which allows said inert gas to be fed on-demand to said heat exchanger and heated, said SCUBA regulator having a refill port, and wherein said heated inert gas evaporates volatile compounds from said specimen to prevent decomposition of said volatile compounds due to exposure to atmospheric gases.

10. A vaporizer apparatus for extracting active ingredients from a specimen of at least one of a crude natural product and an inert particulate matrix, comprising:

a source of ascending hot air provided to heat said specimen to a predetermined temperature wherein said active ingredients of said specimen are volatilized;

a sidearm vent disposed downstream from said source of hot air, to divert said hot air away from said specimen during intermittent periods of vaporizer disuse;

an isolation chamber disposed downstream from said source of hot air, said isolation chamber which isolates said specimen such that particles of said specimen are suspended within a predetermined area by said hot air while said specimen is heated to said predetermined temperature;

a screen provided downstream from said isolation chamber, to filter said particles of said specimen such that said particles are not inhaled by a user after said specimen has been volatilized by application of said hot air within said isolation chamber; and a removable cradle and rod assembly which laterally stabilizes said source of hot air and thus, said sidearm vent, isolation chamber, and screen of said vaporizer apparatus.

11. The vaporizer according to claim 10, wherein said source of hot air comprises a hot air gun.

12. The vaporizer according to claim 10, wherein said isolation chamber further comprises:

a permeable support structure which provides upstream physical support for said unsuspended specimen during apparatus disuse.

13. The vaporizer according to claim 12, wherein said permeable support structure comprises a fritted glass disk.

14. The vaporizer according to claim 10, wherein said screen comprises a meshed material to prevent said suspended particles of said specimen from being inhaled by said user during vaporizer use and prevents downstream loss of suspended particles of said specimen during apparatus use.

15. The vaporizer according to claim 10, wherein said removable cradle and rod assembly comprises:
   a cradle having a rod-receiving channel disposed in a lower portion of said cradle;
   a rod having a rod receiving groove in a center portion of said rod, into which said cradle is disposed; and
   a fastener to removably attach said cradle to said rod, and said cradle to said source of hot air, such that said source of hot air is laterally stabilized.

16. The vaporizer according to claim 15, wherein said source of hot air comprises a hot air gun having a handle to which said cradle and said rod are removably attached.

17. A vaporizer apparatus for extracting active ingredients from a specimen of at least one of a crude natural product and an inert particulate matrix, comprising:
   a high pressure tank to provide an inert gas, said high pressure tank having a demand-type SCUBA regulator and a refill port, wherein said inert gas when heated evaporates volatile compounds from said specimen, to prevent decomposition of said volatile compounds due to exposure to atmospheric gases;
   a heat exchanger which heats said inert gas to a predetermined temperature under thermostatic control;
   an isolation chamber to isolate said specimen such that particles of said specimen are suspended within a predetermined area by said heated inert gas while said specimen is heated to said predetermined temperature; and
   a screen to filter said particles of said specimen such that said particles are not inhaled by a user after said specimen has been volatilized by application of said heated inert gas within said isolation chamber, and prevents downstream loss of suspended particles of said specimen during apparatus use.

18. The vaporizer according to claim 17, further comprising:
   a sidearm vent to divert heated purge gases away from said specimen such that said specimen is not exposed to air, to thereby prevent loss and degradation of said active ingredients of said specimen.

19. The vaporizer according to claim 17, wherein said isolation chamber further comprises:
   a permeable support structure which provides upstream physical support for said unsuspended specimen during apparatus disuse.

20. The vaporizer according to claim 19, wherein said permeable support structure comprises a fritted glass disk.

21. The vaporizer according to claim 17, wherein said screen comprises a meshed material to prevent said suspended particles of said specimen from being inhaled by said user during vaporizer use.

22. A method of extracting active ingredients from a specimen using a vaporizer apparatus, comprising the steps of:
   providing an ascending stream of hot air from a forced hot air source to an isolation chamber provided downstream from said hot air source, to heat the specimen to a predetermined temperature, the specimen being disposed on a permeable support structure within said isolation chamber;
   diverting said hot air away from said isolation chamber during intermittent periods of vaporizer disuse by a user;
   suspending particles of the specimen within said isolation chamber using said hot air, such that said particles are allowed maximum exposure to said extractive hot air flow while simultaneously volatilizing active ingredients of the specimen; and
   filtering said particles from said user such that said user will not inhale said particles of the specimen during vaporizer use.

23. A method of extracting active ingredients from a specimen of at least one of a crude natural product and an inert particulate matrix, using a vaporizer apparatus, comprising the steps of:
   providing inert gas from an inert gas source to a heat exchanger provided downstream from said inert gas source;
   heating said inert gas to a predetermined temperature within said heat exchanger by using a heating band under thermostatic control;
   providing said heated inert gas to an isolation chamber disposed downstream from said hot air source, to heat said specimen to said predetermined temperature, said specimen being disposed on a permeable support structure within said isolation chamber;
   suspending particles of said specimen within said isolation chamber by application of said heated inert gas, such that said particles are allowed maximum exposure to said extractive heated inert gas flow while simultaneously volatilizing active ingredients of said specimen; and
   filtering said particles from said user such that said user will not inhale said particles of said specimen during vaporizer use.

24. The method of claim 23, further comprising the step of:
   purging said heat exchange device of said vaporizer apparatus of atmospheric gases prior to use, when said specimen to be extracted is previously provided.

25. An apparatus for extracting active ingredients from a specimen of at least one of a crude natural product and an inert particulate matrix, comprising:
   a hot air source, operative to provide an ascending stream of hot air to heat said specimen;
   a permeable support structure on which said specimen is placed;
   an isolation chamber containing said permeable support structure, for isolating said specimen while said specimen is heated;
   a filter member for preventing a user from inhaling said specimen during apparatus use; and
   a vent disposed downstream from said source of hot air and upstream of said isolation chamber, to divert said hot air away from said specimen during intermittent periods of vaporizer disuse.

* * * * *

UNITED STATES PATENT AND TRADEMARK OFFICE
CERTIFICATE OF CORRECTION

PATENT NO. : 6,250,301 B1
DATED : June 26, 2001
INVENTOR(S) : David W. Pate

It is certified that error appears in the above-identified patent and that said Letters Patent is hereby corrected as shown below:

<u>Title page,</u>
Item No. [73], Assignee, please change "Hortal Harm B.V." to
-- HortaPharm B.V. --.

<u>Column 5,</u>
Line 46, change "isolation chamber 4" to -- isolation chamber 5 --.

Signed and Sealed this

Eighteenth Day of June, 2002

Attest:

JAMES E. ROGAN
Attesting Officer   Director of the United States Patent and Trademark Office